(12) United States Patent
Wright et al.

(10) Patent No.: US 7,115,571 B1
(45) Date of Patent: Oct. 3, 2006

(54) RETRO-INVERSO PEPTIDES DERIVED FROM INTERLEUKIN-3

(75) Inventors: David E. Wright, Ramona, CA (US); D. Elliott Parks, Del Mar, CA (US)

(73) Assignee: Myelos Corporation, Iselin, NJ (US)

( * ) Notice: Subject to any disclaimer, the term of this patent is extended or adjusted under 35 U.S.C. 154(b) by 650 days.

(21) Appl. No.: 10/048,302

(22) PCT Filed: Jun. 16, 2000

(86) PCT No.: PCT/US00/16759

§ 371 (c)(1), (2), (4) Date: May 7, 2002

(87) PCT Pub. No.: WO00/77028

PCT Pub. Date: Dec. 21, 2000

(51) Int. Cl.
*A61K 38/10* (2006.01)
*A61K 38/16* (2006.01)
*C07K 7/08* (2006.01)
*C07K 14/00* (2006.01)
*C07K 1/00* (2006.01)

(52) U.S. Cl. ............... 514/14; 514/2; 514/12; 514/13; 530/300; 530/324; 530/325; 530/326

(58) Field of Classification Search ............ None
See application file for complete search history.

(56) References Cited

U.S. PATENT DOCUMENTS 4,698,327 A * 10/1987 Nagarajan et al. ............ 514/8
5,376,544 A * 12/1994 Lazarus et al. ............ 435/190
5,699,149 A * 12/1997 Kuroda et al. ............ 356/4.01
5,700,909 A * 12/1997 O'Brien ............ 530/326
6,217,871 B1 * 4/2001 Rose et al. ............ 424/184.1
6,586,403 B1 * 7/2003 Mathison et al. ............ 514/18

FOREIGN PATENT DOCUMENTS

WO WO 9503821 A1 * 2/1995
WO WO 9839357 A1 * 9/1998

OTHER PUBLICATIONS

NA Lokker, et al. J. Immunol. (1991) 146, pp. 893-898.*
J. Rudinger. In: Peptide Hormones, JA Parsons, Ed. (1976) 1-7.*
D. Voet and J.G. Voet. Biochemistry, 2nd Edition.(1995), pp. 235-241.*
D.E. Smilek, et al. Proc. Natl. Acad. Sci. USA (1991) 88, pp. 9633-9637.*
W.S. Messer, "Vasopressin and Oxytocin", web document updated Apr. 3, 2000; <http://www.neurosci.pharm.utoledo.edu/MBC3320/vasopressin.htm>; 5 pages.*
S. Rudikoff, et al. Proc. Natl. Acad. Sci. USA (1982) 79, pp. 1979-1983.*

* cited by examiner

*Primary Examiner*—Bruce R. Campell
*Assistant Examiner*—Andrew D. Kosar
(74) *Attorney, Agent, or Firm*—Kenyon & Kenyon LLP

(57) ABSTRACT

Retro-inverso peptides derived from interleukin-3 (IL-3) having between 12 and about 40 amino acids and including the sequence shown in SEQ ID NO: 1. These peptides have the same activity as native IL-3 and also have neurotrophic activity. Because of the D-amino acid linkage in the peptides, they are less susceptible to proteolytic degradation in vivo.

9 Claims, No Drawings

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: peptide derived from human IL-3

<400> SEQUENCE: 1

Ile Leu Met Glu Asn Asn Leu Arg Arg Pro Asn Leu
1               5                   10

RETRO-INVERSO PEPTIDES DERIVED FROM INTERLEUKIN-3

FIELD OF THE INVENTION

The present invention relates to retro-inverso peptides derived from interleukin-3 (IL-3). These peptides have activities similar to that of the native parent protein, and also have neurotrophic activity.

BACKGROUND OF THE INVENTION

Cytokines are proteins which are produced during the effector phases of natural and specific immunity and serve to mediate and regulate immune and inflammatory responses. Cytokines, like other polypeptide hormones, initiate their action by binding to specific receptors on the surface of target cells. One of the most well known families of cytokines are the interleukins which mediate natural immunity. For a detailed description of the structure and function of the interleukins, see Abbas et al. *Cellular and Molecular Immunology*, W. B. Saunders Company, Philadelphia, pp. 225–243, 1991.

IL-3 acts on numerous target cells within the hematopoietic system. A detailed review of the structure and function of this cytokine may be found in *The Cytokine Handbook*, Third Edition, Thomson, A. Ed., Academic Press, San Diego, Calif., 1998. IL-3 is a glycoprotein having broad structural similarities with other interleukins and hematopoietic growth factors. Murine IL-3 contains 140 amino acids, while human IL-3 contains 133 amino acids. The amino acid sequences of mouse and human IL-3 exhibit only 30% identity, reflecting the lack of cross-species biologic activity (Yang et al., *Cell* 147:3–10, 1986).

IL-3 has the broadest target specificity of any of the hematopoietic growth factors. The range of target cells includes progenitor cells of every lineage derived from the pluripotential hematopoietic stem cells. Thus, IL-3 can stimulate the generation and differentiation of macrophages, neutrophils, eosinophils, basophils, mast cells, megakaryocytes and erythroid cells. In vitro, hematopoietic stem and progenitor cells rapidly die if cultured in tissue culture medium alone. Like other hematopoietic growth factors, IL-3 prevents death by apoptosis and promotes survival in vitro (Williams et al., *Nature* 343:76–79, 1990). When deprived of IL-3, IL-3-dependent cells undergo apoptosis (Williams et al., supra.).

The subcutaneous administration of 2000 $ED_{50}$ units of IL-3 three times a day for three days resulted in an increase in splenic weight and in the number of mast cells and the progenitors of mast cells, neutrophils and macrophages (Schrader et al., *Immune Regulation by Characterized Polypeptides*, Goldstein, G. et al., eds., Liss, New York, pp. 475–484, 1986). The administration of human IL-3 to primates and humans resulted in similar effects to those seen in mice (Donahue et al., *Science* 241:1820–1823, 1988; Mayer et al., *Blood* 74:613–621, 1989). In cynomolgus monkeys, IL-3 induced extramedullary hematopoiesis at sites of subcutaneous injection (Khan et al., *Toxicol. Pathol.* 24:391–397, 1996). IL-3 may have particular utility in stimulating platelet production (Ganser et al., *Blood* 76:666–676, 1990). In addition, clinical trials suggest that sequential administration of IL-3 and G-CSF or GM-CSF may provide optimal stimulation of myelopoiesis (Lemoli et al., *J. Clin. Oncol.* 14:3018–3025, 1996).

Neurotrophins and neurotrophic factors are proteins or peptides capable of affecting the survival, target innervation and/or function of neuronal cell populations (Barde, *Neuron*, 2:1525–1534, 1989). The efficacy of neurotrophins both in vivo and in vitro has been well documented. For example, ciliary neurotrophic factor (CNTF) promotes survival of chicken embryo ciliary ganglia in vitro and supports survival of cultured sympathetic, sensory and spinal motor neurons (Ip et al., *J. Physiol. Paris*, 85:123–130, 1991).

A major obstacle to the in vivo therapeutic use of peptides is their susceptibility to proteolytic degradation. The half-life of intravenously injected IL-3 is short, being on the order of only 40 minutes (Crapper et al., *Immunology* 53:33–42, 1984). Retro-inverso peptides are isomers of linear peptides in which the direction of the sequence is reversed (retro) and the chirality, D or L, of each amino acid is inverted (inverso). There are also partially modified retro-inverso isomers of linear peptides in which only some of the peptide bonds are reversed and the chirality of the amino acid residues in the reversed portion is inverted. The major advantage of such peptides is their enhanced activity in vivo due to improved resistance to proteolytic degradation (For review, see Chorev et al., *Trends Biotech.*, 13:438–445, 1995). Although such retro-inverso analogs exhibit increased metabolic stability, their biological activity is often greatly compromised (Guichard et al., *Proc. Natl. Acad. Sci. U.S.A.*, 91:9765–9769, 1994). For example, Richman et al. (*J. Peptide Protein Res.*, 25:648–662) determined that analogs of linear and cyclic leu-enkephalin modified at the $Gly^3$-$Phe^4$ amide bond had activities ranging from 6%–14% of native leu-enkephalin. Chorev et al., (ibid.) showed that retro-inversion of a peptide which inhibits binding of vitronectin to its receptor resulted in one peptide which was less potent than the parent isomer by a factor of 50,000, and another peptide which was 4,000 fold more potent than the parent cyclic peptide. Guichard et al. (*TIBTECH* 14, 1996), teach that retro-inverso (all-D-retro) antigenic mimicry may only occur with peptides in random coil, loop or cyclic conformations. In the case of "helical" peptide, adequate functional mimicry would be expected only if the helicity was, in fact, absent under the solvent conditions used for assessing antigenic mimicry.

There is a need for IL-3-derived and neurotrophic peptides exhibiting increased metabolic stability while retaining biological activity. The present invention addresses this need.

SUMMARY OF THE INVENTION

One embodiment of the present invention is an isolated retro-inverso peptide having between 12 and about 40 amino acids, wherein said peptide includes the sequence that is retro-inverso with respect to SEQ ID NO: 1, i.e. wherein said peptide comprises the sequence D-Leu-D-Asn-D-Pro-D-Arg-D-Arg-D-Leu-D-Asn-D-Asn-D-Glu-D-Met-D-Leu-D-Ile. In one aspect of this preferred embodiment, at least one basic charged amino acid of said sequence is replaced with a different basic charged amino acid. In another aspect of this preferred embodiment, at least one acidic charged amino acid of said sequence is replaced with a different acidic charged amino acid. Advantageously, at least one non-polar amino acid of said sequence is replaced with a different non-polar amino acid. Preferably, at least one uncharged amino acid of said sequence is replaced with a different uncharged amino acid. In another aspect of this preferred embodiment, at least one aromatic amino acid of said sequence is replaced with a different aromatic amino acid. Advantageously, the peptide is modified at the amino terminus, carboxy terminus, or both amino and carboxy terminus with a moiety independently selected from the group consisting of CH$_3$CO, CH$_3$(CH$_2$)$_n$CO, C$_6$H$_5$CH$_2$CO and H$_2$N(CH$_2$)$_n$CO, wherein n=1–10. Preferably, the peptide is glycosylated. In another aspect of this preferred embodiment, one or more amide bonds of the peptide is reduced. Preferably, one or more nitrogens in said peptide is methylated. In still another aspect of this preferred embodiment, one or more carboxylic acid groups in the peptide is esterified. Preferably, the peptide has the amino acid sequence that is retro-inverso with respect to SEQ ID NO: 1, i.e. wherein said peptide consists of the sequence D-Leu-D-Asn-D-Pro-D-Arg-D-Arg-D-Leu-D-Asn-D-Asn-D-Glu-D-Met-D-Leu-D-Ile.

The present invention also provides a method for promoting neurite outgrowth or myelination in a mammal in need thereof, comprising the step of administering to the mammal an effective, neurite outgrowth or myelination facilitating amount of a composition comprising a retro-inverso peptide having between 12 and about 40 amino acids, wherein the peptide includes the sequence that is retro-inverso with respect to SEQ ID NO: 1, i.e. wherein said peptide comprises the sequence D-Leu-D-Asn-D-Pro-D-Arg-D-Arg-D-Leu-D-Asn-D-Asn-D-Glu-D-Met-D-Leu-D-Ile. Preferably, the peptide has the amino acid sequence that is retro-inverso with respect to SEQ ID NO: 1, i.e. wherein said peptide comprises the sequence D-Leu-D-Asn-D-Pro-D-Arg-D-Arg-D-Leu-D-Asn-D-Asn-D-Glu-D-Met-D-Leu-D-Ile. Advantageously, the mammal is a human. In one aspect of this preferred embodiment, the administering step is direct local injection, systemic, intracranial, intracerebrospinal, topical or oral.

The present invention also provides a method for stimulating hematopoiesis, comprising contacting pluripotential hematopoietic stem cells with an effective, hematopoiesis-stimulating amount of a composition comprising a retro-inverso peptide having between 12 and about 40 amino acids, wherein the peptide includes the sequence that is retro-inverso with respect to SEQ ID NO: 1, i.e. wherein said peptide comprises the sequence D-Leu-D-Asn-D-Pro-D-Arg-D-Arg-D-Leu-D-Asn-D-Asn-D-Glu-D-Met-D-Leu-D-Ile. Preferably, the method results in the generation and differentiation of macrophages, neutrophils, eosinophils, basophils, mast cells, megakaryocytes or erythroid cells.

In another aspect of the present invention, there is provided a retro-inverso peptide having between 12 and about 40 amino acids, wherein said peptide includes the sequence that is retro-inverso with respect to in SEQ ID NO: 1, i.e. wherein said peptide comprises the sequence D-Leu-D-Asn-D-Pro-D-Arg-D-Arg-D-Leu-D-Asn-D-Asn-D-Glu-D-Met-D-Leu-D-Ile, for use in promoting neurite outgrowth or myelination in a mammal. Preferably, the peptide has the amino acid sequence shown in SEQ ID NO: 1. Advantageously, the mammal is a human.

The present invention also provides a retro-inverso peptide having between 12 and about 40 amino acids, wherein the peptide includes the sequence that is retro-inverso with respect to in SEQ ID NO: 1, i.e. wherein said peptide comprises the sequence D-Leu-D-Asn-D-Pro-D-Arg-D-Arg-D-Leu-D-Asn-D-Asn-D-Glu-D-Met-D-Leu-D-Ile, for use in stimulating hematopoiesis of pluripotential hematopoietic stem cells. Preferably, the peptide has the sequence that is retro-inverso with respect to SEQ ID NO: 1, i.e. wherein said peptide comprises the sequence D-Leu-D-Asn-D-Pro-D-Arg-D-Arg-D-Leu-D-Asn-D-Asn-D-Glu-D-Met-D-Leu-D-Ile.

Another embodiment of the present invention is the use of a retro-inverso peptide having between 12 and about 40 amino acids, wherein the peptide includes the sequence that is retro-inverso with respect to SEQ ID NO: 1, i.e. wherein said peptide comprises the sequence D-Leu-D-Asn-D-Pro-D-Arg-D-Arg-D-Leu-D-Asn-D-Asn-D-Glu-D-Met-D-Leu-D-Ile, in the preparation of a medicament for promoting neurite outgrowth or myelination in a mammal in need thereof. Preferably, the peptide has the sequence that is retro-inverso with respect to in SEQ ID NO: 1, i.e. wherein said peptide comprises the sequence D-Leu-D-Asn-D-Pro-D-Arg-D-Arg-D-Leu-D-Asn-D-Asn-D-Glu-D-Met-D-Leu-D-Ile. Advantageously, the mammal is a human.

The present invention also provides the use of a retro-inverso peptide having between 12 and about 40 amino acids, wherein the peptide includes the sequence that is retro-inverso with respect to SEQ ID NO: 1, i.e. wherein said peptide comprises the sequence D-Leu-D-Asn-D-Pro-D-Arg-D-Arg-D-Leu-D-Asn-D-Asn-D-Glu-D-Met-D-Leu-D-Ile, in the preparation of a medicament for stimulating hematopoiesis of pluripotential hematopoietic stem cells in a mammal in need thereof. Preferably, the peptide has the sequence that is retro-inverso with respect to in SEQ ID NO: 1, i.e. wherein said peptide comprises the sequence D-Leu-D-Asn-D-Pro-D-Arg-D-Arg-D-Leu-D-Asn-D-Asn-D-Glu-D-Met-D-Leu-D-Ile. Advantageously, the mammal is a human.

DETAILED DESCRIPTION OF THE PREFERRED EMBODIMENTS

The present invention provides retro-inverso (RI) peptides derived from interleukin-3 (IL-3) which mediate similar effects to native IL-3, including stimulation of hematopoiesis and platelet production. The term "derived from" indicates that the peptides include an active region of interleukin-3, or analogs thereof as defined below. These RI IL-3-derived peptides stimulate the growth and differentiation of macrophages, neutrophils, eosinophils, basophils, mast cells, megakaryocytes and erythroid cells.

These peptides also have therapeutic applications in promoting functional recovery after toxic, traumatic, ischemic, degenerative and inherited lesions to the peripheral and central nervous system. These peptides are also useful for promoting increased myelination and for counteracting the effects of demyelinating diseases. The ability of a particular retro-inverso peptide to mediate an effect similar to the parent peptide can be determined by a person of ordinary skill in the art using standard IL-3 assays as described in the examples below. The use of these peptides will facilitate treatment of various disorders since they will be more stable and easier to synthesize than either the native or recombinant cytokines.

A particular IL-3-derived peptide, from which the retro-inverso peptide of the invention is based is shown in Table 1. The corresponding native (non-retro-inverted) peptides is disclosed in U.S. Pat. No. 5,700,909, the entire contents of which are hereby incorporated by reference.

TABLE 1

| Protein Name | peptide sequence | SEQ ID NO: |
|---|---|---|
| human IL-3 | ILMENNLRRPNL | 1 |

As discussed above, these RI IL-3-derived peptides have the same hematopoietic activities as the corresponding full-length IL-3 protein, and also possess neurotrophic and myelinotrophic activity. One embodiment of the present invention is a method for stimulating the generation and differentiation of pluripotential hematopoietic stem cells into cells such as macrophages, neutrophils, eosinophils, basophils, mast cells, megakaryocytes and erythroid cells by administering to the cells an effective, hematopoiesis-facilitating amount of a RI peptide having between 12 and about 40 amino acids, and encompassing the peptide that is RI with respect to the IL-3-derived peptide shown in SEQ ID NO: 1, or analogs thereof which have similar activity. Such analogs include, for example, replacement of one or more lysine and/or arginine residues with alanine or another amino acid; deletion of one or more lysine and/or arginine residues; replacement of one or more tyrosine and/or phenylalanine residues, deletion of one or more phenylalanine residues and conservative replacements of one or more amino acids within the peptide. The replacement or deletion of lysine/arginine and tyrosine/phenylalanine residues will reduce the susceptibility of peptide degradation by trypsin and chymotrypsin, respectively.

Additional variations of these peptide sequences contemplated for use in the present invention include minor insertions and deletions. Conservative amino acid replacements are contemplated. Such replacements are, for example, those that take place within a family of amino acids that are related in the chemical nature of their side chains. The families of amino acids include the basic charged amino acids (lysine, arginine, histidine); the acidic charged amino acids (aspartic acid, glutamic acid); the non-polar amino acids (alanine, valine, leucine, isoleucine, proline, phenylalanine, methionine, tryptophan); the uncharged polar amino acids (glycine, asparagine, glutamine, cysteine, serine, threonine, tyrosine); and the aromatic amino acids (phenylalanine, tryptophan and tyrosine). In particular, it is generally accepted that conservative amino acid replacements consisting of an isolated replacement of a leucine with an isoleucine or valine, or an aspartic acid with a glutamic acid, or a threonine with a serine, or a similar conservative replacement of an amino acid with a structurally related amino acid will not have a major effect on the properties of the peptide. The ability of any RI peptide comprising the sequence that is retro-inverso with respect to the sequence shown in SEQ ID NO: 1, or insertions, deletions or substitutions thereof, to promote neurite outgrowth, myelination, reverse demyelination and prevent neural cell death can be determined using the assays provided in the examples presented below.

Various chemical modifications will improve the stability, bioactivity and ability of the peptide to cross the blood brain barrier. One such modification is aliphatic amino terminal modification with a derivative of an aliphatic or aromatic acid, forming an amide bond. Such derivatives include, for example, $CH_3CO$, $CH_3(CH_2)_nCO$ (n=1–10), $C_6H_5CH_2CO$, $H_2N.(CH_2)_nCO$ (n=1–10). Another modification is carboxy terminal modification with a derivative of an aliphatic or aromatic amine/alcohol coupled to the peptide via an amide/ester bond. Such derivatives include those listed above. The peptides may also have both amino and carboxy terminal modifications, wherein the derivatives are independently selected from those listed above. The peptides may also be glycosylated, wherein either the alpha amino group or a D-Asn, or both, are modified with glucose or galactose. In another contemplated modification, selected backbone amide bonds are reduced (—NH—$CH_2$). Other modifications include N-methylation of selected nitrogens in the amide bonds and esters in which at least one of the acid groups on the peptide are modified as aromatic or aliphatic esters. Any combination of the above modifications is also contemplated.

Another embodiment of the present invention is a method of facilitating neurite outgrowth in differentiated or undifferentiated neural cells by contacting the cells with an effective, hematopoiesis-facilitating amount of a RI peptide having between 12 and about 40 amino acids, and encompassing the sequence that is retro-inverso with respect to the IL-3-derived peptide shown in SEQ ID NO: 1, i.e. the sequence D-Leu-D-Asn-D-Pro-D-Arg-D-Arg-D-Leu-D-Asn-D-Asn-D-Glu-D-Met-D-Leu-D-Ile, or analogs thereof which have similar activity as described above.

The ability of any such peptide to stimulate neurite outgrowth can easily be determined by one of ordinary skill in the art using the procedures described in Examples 1–9 hereinbelow. The ability of any particular IL-3-derived peptide to mediate the same activity of native IL-3 can be determined using standard assays for the parent peptide as discussed in Examples 10–11.

A typical minimum amount of the RI peptides of the invention for the neurotrophic activity in cell growth medium is usually at least about 5 ng/ml. This amount or more of the RI peptides of the invention for in vitro use is contemplated. Typically, concentrations in the range of 0.1 g/ml to about 10 g/ml of these peptides will be used. Effective amounts for any particular tissue can be determined in accordance with Example 1.

The hematopoietic or neural cells can be treated in vitro or ex vivo by directly administering the RI peptides of the invention to the cells. This can be done, for example, by culturing the cells in growth medium suitable for the particular cell type followed by addition of the peptide to the medium. When the cells to be treated are in vivo, typically in a vertebrate, preferably a mammal, the composition can be administered by one of several techniques. Most preferably, the composition is injected directly into the blood in sufficient quantity to give the desired local concentration of peptide. These RI peptides persist longer in vivo due to the D peptide bonds. In the peptides lacking lysine and arginine residues, proteolytic degradation is reduced. The smaller peptides (i.e. 50-mer or less) will most likely cross the blood brain barrier and enter the central nervous system for treatment of CNS disorders (see Banks et al., *Peptides*, 13:1289–1294, 1992).

For treatment of neural disorders, direct intracranial injection or injection into the cerebrospinal fluid may also be used in sufficient quantities to give the desired local concentration of neurotrophin. In both cases, a pharmaceutically acceptable injectable carrier is used. Such carriers include, for example, phosphate buffered saline and Ringer's solution. Alternatively, the composition can be administered to peripheral neural tissue by direct local injection or by systemic administration. Various conventional modes of administration are contemplated including intravenous, pulmonary, intramuscular, intradermal, subcutaneous, intracranial, epidural, intrathecal, topical and oral. Pharmaceutically acceptable carriers for topical administration include creams, gels, pastes, ointments, lotions, suspensions, emulsions and dispersions.

The peptide compositions of the invention can be packaged and administered in unit dosage form such as an injectable composition or local preparation in a dosage amount equivalent to the daily dosage administered to a patient or as a controlled release composition. A septum sealed vial containing a daily dose of the active ingredient in either PBS or in lyophilized form is an example of a unit dosage. In a preferred embodiment, daily systemic dosages of the RI peptides of the invention based on the body weight of the vertebrate for promoting IL-3 effects such as stimulation of hematopoiesis, and for treatment of neurodegenerative diseases or demyelination diseases, are in the range of from about 0.01 to about 10,000 g/kg. More preferably, daily systemic dosages are between about 0.1 and 1,000 g/kg. Most preferably, daily systemic dosages are between about 10 and 100 g/kg. Daily dosages of locally administered material will be about an order of magnitude less. Oral administration is particularly preferred because of the resistance of the peptides to proteolytic degradation in the gastrointestinal system.

In one preferred embodiment of the invention, the peptides are administered locally to neural cells in vivo by implantation thereof. For example, polylactic acid, polygalactic acid, regenerated collagen, multilamellar liposomes and many other conventional depot formulations comprise bioerodible or biodegradable materials that can be formulated with biologically active neurotrophic peptide compositions. These materials, when implanted, gradually break down and release the active material to the surrounding tissue. The use of bioerodible, biodegradable and other depot formulations is expressly contemplated in the present invention. Infusion pumps, matrix entrapment systems and combinations with transdermal delivery devices are also contemplated. The peptides may also be encapsulated within a polyethylene glycol conformal coating as described in U.S. Pat. No. 5,529,914 prior to implantation.

The peptides of the invention may also be enclosed in micelles or liposomes. Liposome encapsulation technology is well known. Liposomes may be targeted to specific tissue, such as neural tissue, through the use of receptors, ligands or antibodies capable of binding the targeted tissue. The preparation of these formulations is well known in the art (Radin et al., $Meth.$ $Enzymol.$, 98:613–618, 1983).

There are currently no available pharmaceuticals able to promote full functional regeneration and restoration of the structural integrity of neural systems. This is particularly true of the CNS. Any degree of regeneration of peripheral nerves through the use of neurotrophic factors is within the scope of this invention. Moreover, neurotrophic factors can be therapeutically useful in the treatment of neurodegenerative diseases associated with the degeneration of neural populations or specific areas of the brain. Any degree of retardation or halting or reversing such degeneration is within the scope of the present invention. The principal cause of Parkinson's disease is the degeneration of dopaminergic neurons of the substantia nigra. The RI peptides of the invention may be therapeutically useful in the treatment of Parkinson's disease. Retinal neuropathy, an ocular neurodegenerative disorder leading to loss of vision in the elderly, is also treatable using the RI peptides of the invention.

It has long been believed that in order to reach neuronal populations in the brain, neurotrophic factors would have to be administered intracerebrally since these proteins do not cross the blood brain barrier. U.S. Pat. No. 5,571,787 discloses that an iodinated neurotrophic 18-mer fragment derived from saposin C crosses the blood brain barrier. Thus, the RI peptides having up to about 22 amino acids will also cross this barrier and can thus be administered intravenously. Other neuronal populations, such as motor neurons, can also be treated by intravenous injection, although direct injection into the cerebrospinal fluid is also envisioned as an alternate route.

Cells may be treated to facilitate myelin formation or to prevent demyelination in the manner described above in vivo, ex vivo or in vitro. Diseases resulting in demyelination of nerve fibers including MS, acute disseminated leukoencephalitis, trauma to brain and/or spinal cord, progressive multifocal leukoencephalitis, metachromatic leukodystrophy, adrenal leukodystrophy and maldevelopment of the white matter in premature infants (periventricular leucomalacia) can be slowed or halted by administration of the neurotrophic peptides of the invention to the cells affected by the disease.

The RI IL-3-derived peptide compositions of the present invention can also be used to support hematopoieses, to enhance the survival of cultured motor neurons and to determine the effects of neurotrophic factors and myelin facilitating materials. However, more practically, they have an immediate use as laboratory reagents and components of cell growth media in order to facilitate hematopoiesis and maintain neural cells in vitro.

The peptides of the invention are synthesized using an automated solid-phase protocol well known in the art. All peptides are purified by high performance liquid chromatography (HPLC) on a reverse-phase column to an extent greater than about 95% prior to use.

The following examples are merely illustrative and are not intended to limit the scope of the present invention.

Example 1

Stimulation of Neurite Outgrowth

NS20Y neuroblastoma cells are grown in DMEM containing 10% fetal calf serum (FCS). Cells are removed with trypsin and plated in 30 mm petri dishes onto glass coverslips. After 20–24 hours, the medium is replaced with 2 ml DMEM containing 0.5% FCS plus 0, 0.5, 1, 2, 4 or 8 ng/ml of a RI IL-3-derived peptide having between 12 and about 40 amino acids and including the sequence that is retro-inverso with respect to SEQ ID NO: 1. Cells were cultured for an additional 24 hours, washed with PBS and fixed with Bouin's solution (saturated aqueous picric acid/formalin/acetic acid 15:5:1) for 30 minutes. Fixative was removed with PBS and neurite outgrowth was scored under a phase contrast microscope. Cells exhibiting one or more clearly defined neurites equal to or longer than one cell diameter were scored as positive. At least 200 cells were scored in different portions of each dish to determine the percentage of neurite bearing cells and assays were performed in duplicate.

Example 2

Prevention of Cell Death

NS20Y cells are plated as described in Example 1 and grown on glass coverslips in 0.5% fetal bovine serum for 2 days in the presence or absence of 8 ng/ml of an RI IL-3-derived peptide having between 12 and about 40 amino acids and including the sequence that is retro-inverso with respect to SEQ ID NO: 1. Media is removed and 0.2% trypan blue in PBS is added to each well. Blue-staining dead cells are scored as a percentage of the total on an inverted microscope, counting 400 cells in four areas of each well. The average error of duplicates was 5%.

Example 3

Promotion of Neurite Outgrowth Ex Viva

Dorsal root ganglia are removed from adult rats and sensory neurons were prepared as described by Kuffler et al. ($J.$ $Neurobiol.$ 25:1267–1282, 1994). Neurons are treated with 0.5 ng/ml of an RI IL-3-derived peptide having between 12 and about 40 amino acids and including the sequence that is retro-inverso with respect to SEQ ID NO: 1. After three days of treatment, the length of the longest neuritic projections are measured on a micrometer grid. The longest neurites in neurons treated with RI peptide are approximately three times longer than those treated with a control (non-RI) peptide or in untreated controls. After a 48 hour treatment, all cells respond similarly to nerve growth factor (NGF) in that extensive branching is observed. These results indicate that the IL-3-derived peptides promote the differentiation of sensory neurons.

Example 4

Reversal of Demyelination in a Rat Model

Experimental allergic encephalomyelitis (EAE) is a rat model of human multiple sclerosis (MS). In rats, EAE is induced by injecting foreign protein (guinea pig spinal cord) which results in inflammation and demyelination in white matter 11 days later. This demyelination resembles that seen in actively demyelinating human MS lesions (Liu et al., *Multiple Sclerosis* 1:2–9, 1995).

EAE is induced in Lewis rats by injection of an emulsion of guinea pig spinal cord and complete Freund's adjuvant (CFA). At day 14, when weakness is evident, treatment with a RI IL-3-derived peptide having between 12 and about 40 amino acids, and including the sequence that is retro-inverso with respect to SEQ ID NO: 1, is begun (200 g/kg intramuscularly) and continued for 8 days every day. Six rats are injected with vehicle only. Stride length, a measure of muscle weakness, is scored on days 14 and 22. In addition, the number and size of demyelinating lesions (plaques) in the spinal cord at day 22 per $mm^2$ is scored. Lastly, the amount of cholesterol ester in brain, a marker of myelin breakdown, is scored at day 22.

The stride length of both groups is decreased at day 14, whereas after treatment for 8 days, the IL-3-derived peptide-treated animals return to normal, but the vehicle treated animals do not. A significant reduction of cholesterol ester content is observed in the brains of the treated group. Moreover, the number of spinal cord lesions is significantly reduced after 10 days of treatment with IL-3-derived peptide. Lastly, the average lesion size is significantly reduced. There is no difference in weight loss between the control and experimental animals. These results indicate a significant clinical, biochemical and morphological reversal of EAE after systemic treatment with IL-3-derived peptides. This action differs from the anti-inflammatory effect of current MS drugs which do not act directly upon myelin repair.

Example 5

Ex Vivo Myelination Assay

Newborn mouse cerebellar explants are prepared according to Satomi (*Zool. Sci.* 9:127–137, 1992). Neurite outgrowth and myelination are observed for 22 days in culture, during the period when the newborn mouse cerebellum normally undergoes neuronal differentiation and myelination begins. An RI IL-3-derived peptide having between 12 and about 40 amino acids, and including the sequence that is retro-inverso with respect to SEQ ID NO: 1, is added on the second day after preparation of the explants (three control and three treated explants) and outgrowth of neurites and myelination are assessed under a bright field microscope with a video camera. Saposin C is used as a positive control at a concentration of between about 1 and 10 g/ml. Myelination is stimulated by the IL-3-derived peptides to a similar extent as with saposin C.

Alternatively, myelination may be assayed by incorporation of $^{35}S$ into sulfolipids which are exclusive to myelin as described below.

Example 6

Incorporation of $^{35}S$ into Sulfolipids

Primary myelin-containing Schwann cells are incubated in low sulfate media (DMEM) containing 0.5% fetal bovine serum (FBS), followed by addition of $^{35}S$-methionine and an RI IL-3-derived peptide having between 12 and about 40 amino acids, and including the sequence that is retro-inverso with respect to SEQ ID NO: 1, for 48 hours. Saposin C is used as a positive control. Cells are rinsed with PBS, harvested and sonicated in 100 1 distilled water. An aliquot of cell lysate is removed for protein analysis and the remainder is extracted with 5 ml chloroform/methanol (2:1, v/v). Lipid extracts are chromatographed and immunostained with anti-sulfatide monoclonal antibody as described (Hiraiwa et al., *Proc, Natl. Acad Sci U.S.A.* 94:4778–4781). Similar amounts of sulfatide are observed after peptide and saposin C treatment.

Example 7

Use of RI Peptides in Treating Traumatic Ischemic CNS Lesions

Humans with traumatic lesions to the brain or spinal cord receive systemic injections of about 100 g/kg of an RI IL-3-derived peptide having between 12 and about 40 amino acids, and including the sequence that is retro-inverso with respect to SEQ ID NO: 1, in a sterile saline solution or in depot form. Improvement is assessed by gain of sensory or motor nerve function (i.e. increased limb movement). Treatments continue until no further improvement occurs.

Example 8

Use of RI Peptides in Treating Demyelination Disorders

Patients diagnosed with early stage MS are given an RI IL-3-derived peptide having between 12 and about 40 amino acids, and including the sequence that is retro-inverso with respect to in SEQ ID NO: 1, by systemic injection using the same dose range as in Example 7. Dosages are repeated daily or weekly and improvement in muscle strength, musculoskeletal coordination and myelination (as determined by MRI) is observed. Patients with chronic relapsing MS are treated in the same manner when subsequent relapses occur.

Typically, IL-3 is assayed by its ability to stimulate the formation of colonies of differentiated cells from progenitor cells of the bone-marrow in soft agar. Alternatively, IL-3 can be assayed for its proliferative effect on cell lines derived from human leukemias such as TF-1 and MO-7e. Detailed protocols for IL-3 assays may be found in *Cytokines, a Practical approach*, Balkwill, F., ed., IRL Press, New York, second edition, 1995, pp. 247–268, 372–377, the entire contents of which are incorporated be reference. IL-3 assay protocols are provided in the following example.

Example 9

IL-3 Colony Formation Assay

IL-3 stimulates the formation of mixed colonies of different cell types. Colonies of more than 50 cells are counted and analyzed after 7–14 days by eye using a binocular microscope. The number of colonies is usually related to the specific activity or concentration of IL-3 in the agar culture. Morphological analysis by staining of dried and fixed gels allows proper identification of the colony type (Metcalf, *The Hemopoietic Colony Stimulating Factors*, Elsevier Press, Amsterdam, 1984).

Cell suspensions are prepared from human bone marrow by collecting bone-marrow aspirates in sterile tubes containing 5–10 ml of Iscove's modified Dulbecco's medium (IMDM) plus 400 units of preservative-free heparin. Cells are centrifuged at 600–1,000×g for 10 min, the supernatant is discarded and the cells are resuspended in IMDM plus 2% fetal calf serum (FCS), then mixed gently by pipetting. Cells are counted in a hemacytometer and the concentration is adjusted as needed. As the cellularity of bone-marrow aspirates varies with the pathology of the patient, and also with the aspiration technique, some judgment must be exercised about the volume used to resuspend the cells. Hypocellular marrow samples are resuspended in 1–2 ml, but usually 5–10 ml are used. Cell suspensions are kept on ice until plating.

The following protocol details the steps for the assay of Mix-CFC from human bone marrow. This assay allows the growth of mixed colonies, which may contain several myeloid lineages (neutrophils, eosinophils, basophils, erythroid cells, monocytes-macrophages and megakaryocytes) resulting from clonal proliferation of Mix-CFC. Three aliquots of 1 ml containing $5 \times 10^4$ human bone marrow cells each are placed in 3 cm diameter Petri dishes. The plating mixture is made as follows, to a total value of 3.3 ml (to allow 0.3 ml for waste):

| Component | Vol (%) | For 3.3 ml |
| --- | --- | --- |
| Cell suspension (10X desired final concentration) | 10 | 0.33 |
| BSA (10% stock solution) | 10 | 0.33 |
| IL-3 RI peptide or cond. medium | 10 | 0.33 |
| Fetal calf serum | 20 | 0.66 |
| Erytoropoietin (2 units) | 2 | 0.066 |
| IMDM | 48 | 1.32 |

The agar (3.3%) is placed into a boiling water bath to melt. While the agar is melting, the plating mixture may be warmed to 37 C in a water bath to prevent the agar from setting too quickly when added. Agar (0.30 ml) is added, mixed thoroughly but gently, and 1 ml is plated per dish. Dishes are placed on a tray and allowed to set. The dishes can be placed in a refrigeration for about 2 min. to speed the process. The plates are then placed into a fully humidified gas incubator at 37 C and incubated for 14 days. Colonies are scored under about 40× magnification using a microscope with a zoom lens, or an inverted microscope. Individual colonies are picked up for cytological examination using a Pasteur pipette and suspended in 0.1 ml of medium (plus a source of protein, either 1% serum or 0.1% BSA, for standard cytospin preparations.

Example 10

IL-3 Cell Proliferation Assay

Several IL-3-dependent cell lines can be employed to determine whether a peptide has IL-3 activity. The cell lines FDCP-1, FDCP-2, 32DCL23, TF-1 (human erythroleukemia), AML-193 (human acute myeloid leukemia; ATCC CRL 9589); MO-7e (human megakaryoblastic leukemia) and DAM1 (human megakaryoblastic cells; Chen et al., *Br. J. Haematol.* 88: 481–490, 1994) are all IL-3-dependent. To determine whether a particular RI IL-3-derived peptide having between 12 and about 40 amino acids, and including the sequence that is retro-inverso with respect to in SEQ ID NO: 1, has IL-3 activity, the peptide or analog thereof such as a peptide having one or more conservative amino acid replacements, is assayed for IL-3 activity by incubation with cells as follows:

Cells are cultured in suspension until they reach an exponential growth rate, then harvested by spinning at 800×g for 5 minutes on a bench centrifuge using a swing-out rotor. The cell pellet is suspended in the appropriate medium, centrifuged again, and resuspended a further two times. Cells are resuspended at a concentration of $1-2 \times 10^6$ /ml in Fischer's medium (Gibco-plus glutamine) plus horse serum (10% v/v) and plated out in a total volume of 100 I at trial concentrations of $1-2 \times 10^5$ cells/ml with either dilutions of the RI IL-3-derived peptide under test or dilutions of a standard preparation of IL-3. The final concentration of horse serum (or, if the cells are normally cultured in it, fetal calf serum) is 10–20% (v/v). Cells are incubated in a $CO_2$ incubator at 37 C.

After 24 or 48 hours, the effects of the growth factors on survival and proliferation are assessed using the Trypan blue exclusion assay in which the cell suspension is mixed 1:1 with Trypan blue solution and the viable cells which exclude the dye are counted. Another method for assessment of cell proliferation (DNA synthesis) involves the measurement of [$^3$H]thymidine incorporation. After 24 or 48 hours, [$^3$H] thymidine (37 kBq) is added to each well and the incubation continued for 4 hours. The cells are removed from the incubator and serially transferred to GF/C filters on a Millipore cell harvester or similar apparatus. The cells are washed three times with trichloroacetic acid (TCA) and the TCA-precipitable material retained on the filter counted in a liquid scintillation counter. The relative growth promoting activities of the standard and the diluents of the RI IL-3-derived peptides are compared to quantify the growth promoting activity of the RI IL-3-derived peptides.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A retro-inverso peptide having between 12 and about 40 amino acids, wherein said peptide comprises the sequence D-Leu-D-Asn-D-Pro-D-Arg-D-Arg-D-Leu-D-Asn-D-Asn-D-Glu-D-Met-D-Leu-D-Ile.

2. The retro-inverso peptide of claim 1, wherein the peptide consists of the sequence D-Leu-D-Asn-D-Pro-D-Arg-D-Arg-D-Leu-D-Asn-D-Asn-D-Glu-D-Met-D-Leu-D-Ile.

3. The retro-inverso peptide of claim 1, wherein said peptide is optionally modified, said modification selected from a group consisting of glycosylation, reduction of one or more amide bonds, methylation of one or more nitrogens, esterification of one or more carboxylic acid groups, and modification at the amino terminus, carboxy terminus, or both amino and carboxy termini with a moiety independently selected from the group consisting of $CH_3CO$, $CH_3(CH_2)_nCO$, $C_6H_5CH_2CO$ and $H_2N(CH_2)_nCO$, wherein n=1–10.

4. The retro-inverso peptide of claim 3, wherein the peptide consists of the sequence D-Leu-D-Asn-D-Pro-D-Arg-D-Arg-D-Leu-D-Asn-D-Asn-D-Glu-D-Met-D-Leu-D-Ile.

5. A composition comprising a retro-inverso peptide having between 12 and about 40 amino acids, wherein said peptide comprises the sequence D-Leu-D-Asn-D-Pro-D-Arg-D-Arg-D-Leu-D-Asn-D-Asn-D-Glu-D-Met-D-Leu-D-Ile.

6. The composition of claim 5, wherein said retro-inverso peptide consists of the sequence D-Leu-D-Asn-D-Pro-D-Arg-D-Arg-D-Leu-D-Asn-D-Asn-D-Glu-D-Met-D-Leu-D-Ile.

7. A composition comprising the retro-inverso peptide of claim 1 and a pharmaceutically acceptable carrier.

8. A composition comprising the retro-inverso peptide of claim 3 and a pharmaceutically acceptable carrier.

9. A composition comprising the retro-inverso peptide of claim 3 and a pharmaceutically acceptable carrier.

* * * * *